(12) United States Patent
Schneider et al.

(10) Patent No.: US 9,031,360 B2
(45) Date of Patent: May 12, 2015

(54) FLEXIBLE OPTICAL CIRCUIT

(71) Applicant: Tyco Electronics Nederland BV, 's-Hertogenbosch (NL)

(72) Inventors: Paul Schneider, Gemonde (NL); Sander Dorrestein, Helmond (NL)

(73) Assignee: Tyco Electronics Nederland BV (NL)

( * ) Notice: Subject to any disclaimer, the term of this patent is extended or adjusted under 35 U.S.C. 154(b) by 177 days.

(21) Appl. No.: 13/623,360

(22) Filed: Sep. 20, 2012

(65) Prior Publication Data
US 2013/0077913 A1    Mar. 28, 2013

Related U.S. Application Data

(60) Provisional application No. 61/538,737, filed on Sep. 23, 2011.

(51) Int. Cl.
*G02B 6/12* (2006.01)
*G02B 6/36* (2006.01)
*A61M 16/06* (2006.01)

(52) U.S. Cl.
CPC ......... *G02B 6/3612* (2013.01); *A61M 16/0666* (2013.01); *A61M 16/0683* (2013.01)

(58) Field of Classification Search
USPC ................................................. 385/14, 147
See application file for complete search history.

(56) References Cited

U.S. PATENT DOCUMENTS

| | | | | |
|---|---|---|---|---|
| 3,674,914 A | * | 7/1972 | Burr | 174/261 |
| 5,813,148 A | * | 9/1998 | Guerra | 36/137 |
| 5,996,927 A | * | 12/1999 | Weirauch et al. | 242/556.1 |
| 7,233,712 B2 | * | 6/2007 | Arellano | 385/14 |

FOREIGN PATENT DOCUMENTS

EP    0 679 914    * 11/1995    ............... G02B 6/36

* cited by examiner

*Primary Examiner* — Uyen Chau N Le
*Assistant Examiner* — Chad Smith
(74) *Attorney, Agent, or Firm* — Saul Ewing LLP

(57) ABSTRACT

A process of manufacturing an optical flexible circuit comprising: (a) disposing an adhesive layer on at least a portion of a carrier film, said adhesive layer having a downward adhesive face and an upward adhesive face, said downward adhesive face and said carrier film being configured such that said carrier film is removable from said downward adhesive face without disruption of said downward adhesive face; (b) routing one or more fibers on said upward adhesive layer; (c) coating said fibers to define an optical circuit; and (d) optionally parting said carrier film to separate said optical circuit from other optical circuits on said carrier film.

16 Claims, 4 Drawing Sheets

FLEXIBLE OPTICAL CIRCUIT

REFERENCE TO RELATED APPLICATION

This application claims priority to U.S. Provisional Application No. 61/538,737 filed Sep. 23, 2011, incorporated herein by reference, including its appendix entitled "Fibre Optic Circuits" by Paul Schneider and Sander Dorrestein.

FIELD OF INVENTION

The subject matter herein relates generally to optical circuits, and more particularly, to flexible optical circuits.

BACKGROUND OF INVENTION

The need for increased bandwidth is straining the architecture of fiber optic infrastructure. With an ever increasing amount of optical transmission, fiber management is more challenging than ever before. Fiber switching and cross connects add to this complexity as does the density of the individual fiber management systems. The increasing number of patch cords and fan-out cables required to connect modem infrastructure is problematic not only from a cable management perspective, but also from an operations standpoint (e.g., cooling).

One approach to solve this problem is a low cost fiber interconnect system that can handle complex optical cross connects and reduce space. This space reduction is essential as high data rate processors are requiring more energy, and cooling these processors becomes critical to maintain the system reliability and performance.

A preferred low cost interconnect system is a fiber optical flex circuit (OFX). Such circuits comprise of a number of individual fibers which have been precisely positioned into a predetermined form or pattern, and fixed in place using a special coating designed to bond the fibers together in position. In some applications, the fibers are disposed on a sheet of thermally-stable material (e.g., Kapton) allowing these circuits to withstand a wide temperature range of −40 to +85° C. These thin foils are very efficient in terms of space saving and structured fiber management. Such fiber circuits can route fibers in almost any pattern, and therefore offer a solution to most fiber management problems. The most common applications include fiber on the board, board to board, back bone cross connections, and harsh military and aerospace applications.

Although use of flexible optical circuits reduces space requirements, Applicant recognizes that space is so limited in many applications that often securing such optical circuits to a cabinet or other framework is problematic. For example, securing these optical circuits traditionally requires the use of clips or other mechanical devices. However, limitations in space may interfere with the use of such devices. Accordingly, there is a need for a flexible optical circuit that can be secured in place without the need for bulky and clumsy mechanical devices. The present invention fulfills this need among others.

SUMMARY OF INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

The present invention provides a flexible optical circuit having an adhesive bottom that can be readily affixed to a surface during installation. Applicant recognizes that the traditional process of preparing flexible optical circuits can be modified without substantial change to existing production machinery to provide an adhesive portion on the underside of the optical circuit.

Accordingly, one aspect of the present invention is a process of manufacturing an optical flexible circuit having an adhesive surface for affixing the circuit during installation. In one embodiment, the process comprises: (a) disposing an adhesive layer on at least a portion of a carrier film, the adhesive layer having a downward adhesive face and an upward adhesive face, the downward adhesive face and the carrier film being configured such that the carrier film is removable from the downward face without disruption of the downward adhesive face; (b) routing one or more fibers on the upward adhesive layer to define an optical circuit; (c) coating the fibers; and (d) optionally parting the carrier film to separate the optical circuit from other optical circuits on the carrier film.

Anther aspect of the present invention is a flexible optical circuit having an adhesive bottom surface for affixing to a surface during installation. In one embodiment, the optical flexible circuit comprises: (a) a removable carrier film; (b) an adhesive layer on at least a portion of a carrier film, the adhesive layer having a downward adhesive face and an upward adhesive face, the downward adhesive face and the carrier film being configured such that the carrier film is removable from the downward face without disruption of the downward adhesive face; (c) one or more fibers routed on the upward adhesive layer to define an optical circuit; and (d) a coating over the fibers.

Yet another aspect of the invention is the process of affixing the optical circuit to a surface during installation. In one embodiment, the process comprises: (a) removing the carrier film from the downward adhesive layer to expose the downward adhesive face; and (b) affixing the downward adhesive face to a surface to secure the optical circuit to the surface.

DETAILED DESCRIPTION

Figure 1:
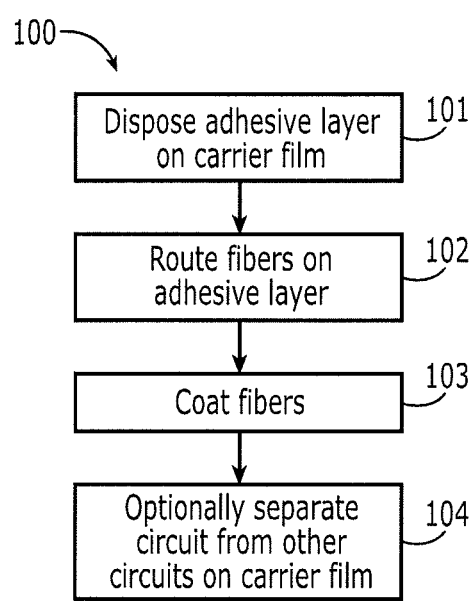
FIG. 1 is a flow chart of one embodiment of the present invention.
Figure 5:
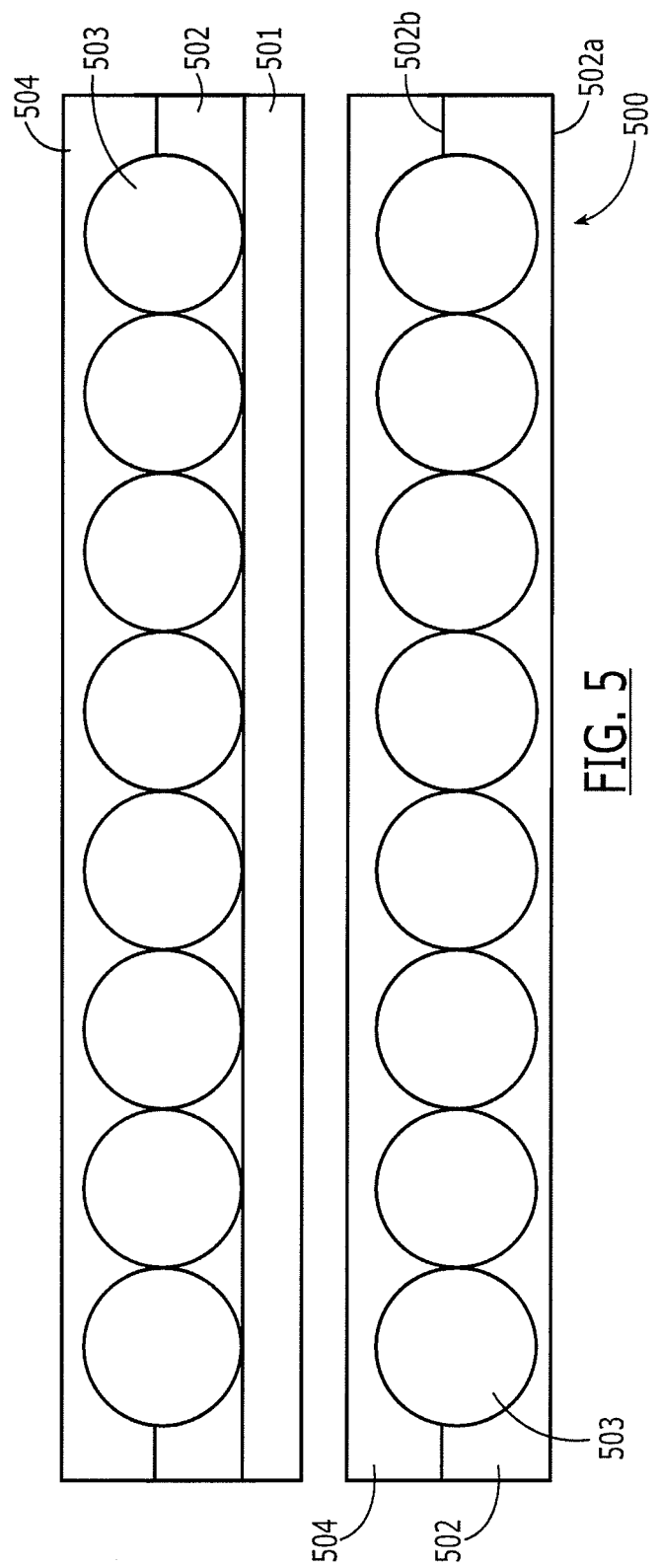
FIG. 5 shows an optical circuit of the present invention with the carrier film in place and with the carrier film removed.

Referring to FIGS. 1 and 5, one embodiment of the process 100 of manufacturing an optical flexible circuit of the present invention and one embodiment of a flexible optical circuit 500 of the present invention are shown, respectively. First, in step 101, an adhesive layer 502 is disposed on at least a portion of a carrier film 501. The adhesive layer 502 has a downward adhesive face 502a and an upward adhesive face 502b. The downward adhesive face 502a and the carrier film 501 are configured such that the carrier film 501 is removable from the downward face without disruption of the downward adhesive face. In step 102, one or more fibers 503 are routed on the upward adhesive layer 502b. Next, in step 103, a coating 504 is disposed over the fibers to secure them in place, thus defining an optical circuit 500. Optionally, in step 104, the optical circuit 500 is parted from other optical circuits on the carrier film 501.

The flexible optical circuit 500 prepared from method 100 is adapted for easy installation. Referring to FIG. 5, in one embodiment, the method of installation comprises removing the carrier film 501 from the downward adhesive face 502a to expose the downward adhesive face 502a, and affixing the downward adhesive face to a surface (not shown) to secure the optical circuit to the surface. These elements of the present invention are discussed in greater detail below.

It should be appreciated that, throughout this disclosure, relative terms such as upward and downward are used. Such terms are intended to be illustrative of the invention and to indicate relative positions within the circuit itself. Such terms are not intended to be restrictive in the manufacture or use of the circuit. For example, it is within the scope of the invention that the circuit be installed up-side-down, such that the downward facing adhesive layer is facing upward and is adhered to a ceiling or similar structure.

Figure 2:
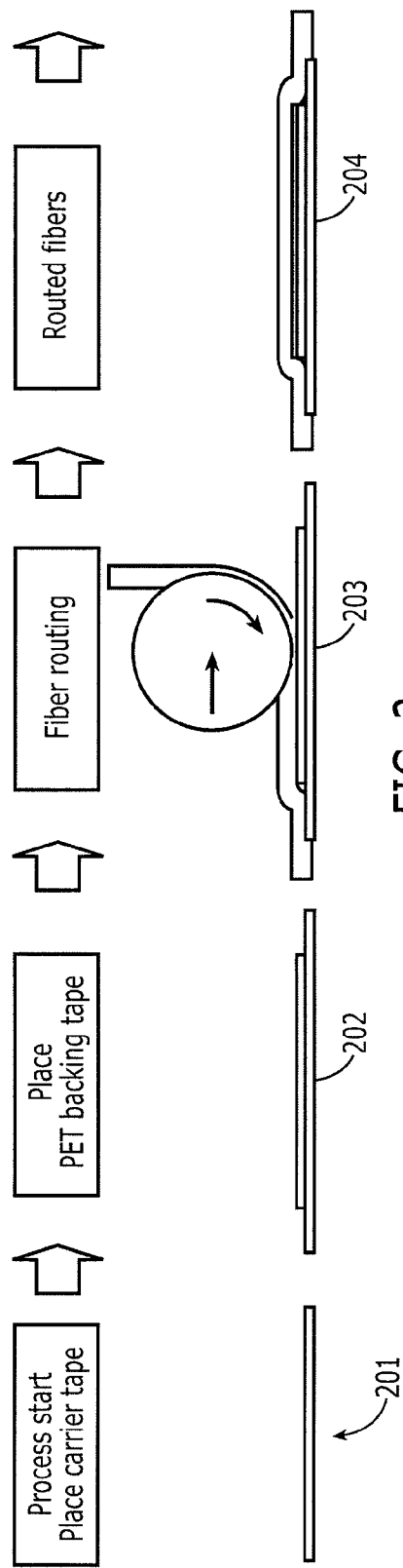
FIG. 2 shows process steps of routing fibers according to the present invention.
Figure 3:
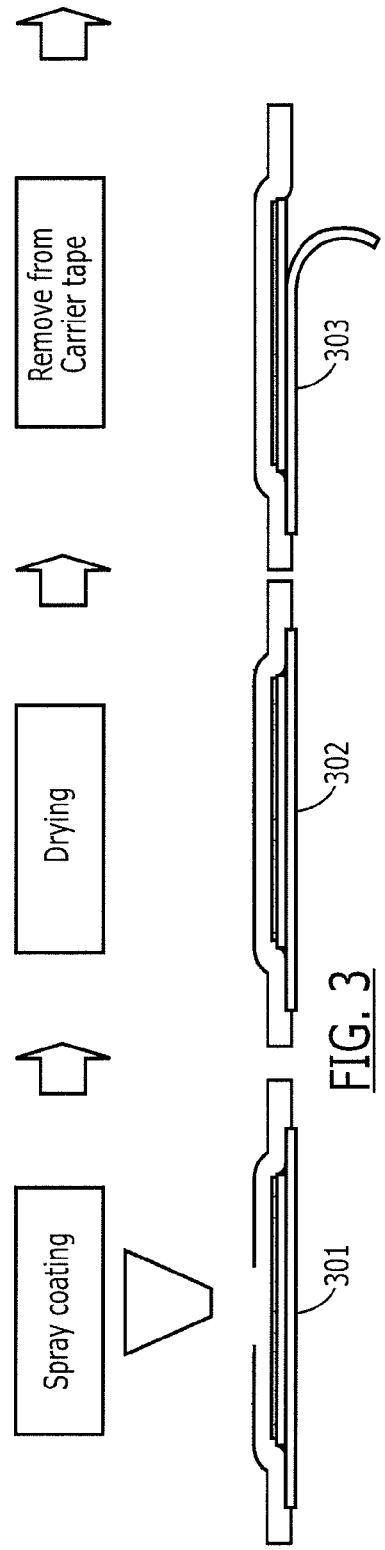
FIG. 3 shows process steps of coating the routed fibers according to the present invention.

Referring to FIGS. 2 and 3, in one embodiment, the manufacturing of optical flex circuits comprises two major process steps: (1) fiber routing on the carrier/adhesive layer; and (2) application of conformal coating on the fibers.

Considering first fiber routing, in one embodiment, the process starts with providing the carrier film in step 201 and then applying the adhesive layer in step 202. The carrier film serves several functions: it maintains the position of the fibers for straight tails; it positions the adhesive layer; and it protects the downward adhesive face of the adhesive layer until the circuit is ready for installation (at which point the carrier film is removed to expose the downward adhesive face for affixing to a structure as mentioned above). In one embodiment, the carrier film has a thin adhesive sufficiently strong to maintain fiber position in straight lines. However, the adhesion of the carrier film must be low enough that during installation of the optical circuit, the film may be peeled off without disturbing the fibers or the downward adhesive face.

On the other hand, the adhesive layer requires strong adhesive characteristics to maintain the position of fibers in curved paths, tight turns, and crossings. The challenge facing fiber routing is to maintain the position of fibers directly after routing and after coating. Maintaining the position of the fibers is especially critical during the fiber routing before the optional coating is applied to the circuit. A bent fiber builds up stress, the tighter the bend-the higher the stress in the fiber. The adhesive layer must to be capable to withstand the force applied by the fiber after routing.

One of skill in the art can readily determine the appropriate adhesive to use on the carrier film and the adhesive layer in light of this disclosure. For example, the adhesive layer may be a film acrylic pressure-sensitive, solvent-resistance adhesive system. Such a system features high ultimate bond strength with excellent high temperature performance and excellent solvent resistance. Furthermore, bond strength for this specific adhesive system increases substantially with natural aging. The thickness of the adhesive layer may vary with the application, although a thick layer (e.g., 100-140 um) has provided good results. In one embodiment, double-sided tape is used. For example, a PET or Kapton foil with adhesive on both sides may be used. Alternatively, the adhesive layer may be homogeneous with no foil or substrate used.

Figure 4:
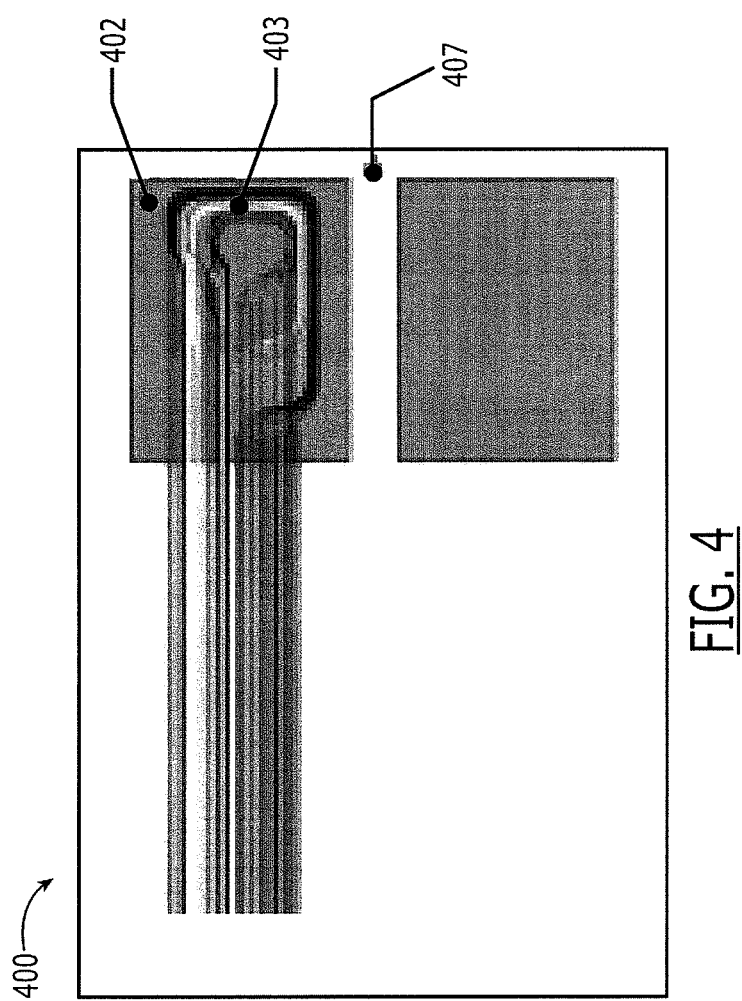
FIG. 4 shows a top view of an optical circuit prior to coating.

In step 203, in one embodiment, the fiber is placed on the upper adhesive face by a guiding needle at given force and speed. In one embodiment, the fiber routing pattern is designed in CAD software and converted by CAM into a CNC program that controls the path of the needle. An uncoated optical circuit is provided in step 204. One embodiment of the uncoated optical circuit 400 is shown in FIG. 4. As shown, the adhesive layer 402 is deposited on the carrier film 401 in discrete patches, leaving portions of the carrier film exposed. The optical fibers 403 overlay both the exposed portions of the carrier film and the adhesive layer.

In one embodiment, after the routing process, the noncoated product is transferred to a coating machine to coat the fibers and the carrier with a conformal coating in step 301. This coating may be applied in different ways. In one embodiment, it is sprayed onto the surface of the adhesive layer, the carrier film, and the optical fibers. This spray can be controlled accurately to maintain an exact layer of coating over the entire surface. The thickness of this layer may vary depending on the intended use of the circuit. In one embodiment, the entire upper adhesive face is covered with the conformal coating. This serves to protect the fibers, and improves the adhesion of the fibers to the adhesive layer. Furthermore, the conformal coating covered exposed adhesive on the adhesive layer to prevent it from adhering to dirt and debris and other unintended objects.

In one embodiment, the fiber tails on the carrier film are also covered with the same conformal coating, thereby encasing the loose fibers and forming a ribbon cable. This ribbon cable may be spliced with other fibers or terminated with connectors as is known in the art.

The conformal coating may be any material known to coat and protect while remaining flexible. For example, in one embodiment, the conformal coating is a silicon-based material, such as those commonly used in the electronics industry to protect electrical circuit boards from the elements. The silicon material provides a strong adhesion to the optical fibers, providing a durable final product that can withstand harsh environmental conditions.

In one embodiment, once the surface is coated, coating is allowed to cure in step 302. Different curing procedures, such as UV and air drying, may be used. After this curing process, the optical circuit can be terminated with connectors or spliced directly with other fibers as the application dictates. During installation, the carrier film can be removed from the product in step 303 and the fiber circuit affixed to a surface as described above.

While this description is made with reference to exemplary embodiments, it will be understood by those skilled in the art that various changes may be made and equivalents may be substituted for elements thereof without departing from the scope. In addition, many modifications may be made to adapt a particular situation or material to the teachings hereof without departing from the essential scope. Also, in the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

What is claimed is:

1. A process of manufacturing an optical flexible circuit comprising:
    (a) providing a carrier film, a portion of said carrier film being covered with an adhesive layer, said adhesive layer having a downward adhesive face and an upward adhesive face, said downward adhesive face and said carrier film being configured such that said carrier film is removable from said downward adhesive face, said adhesive layer covering only a portion of said carrier film, leaving an exposed portion of said carrier film;
(b) disposing a plurality of fibers on said carrier film in a pattern comprising at least one curved portion in which said fibers are curved, and at least one tail portion in which said fibers are essentially straight, said curved portion being disposed on said adhesive layer and said tail portion being disposed on said exposed portion;
(c) coating said fibers to define an optical circuit; and
(d) optionally parting said carrier film to separate said optical circuit from other optical circuits on said carrier film.

2. The process of claim 1, wherein said adhesive layer is double sided tape.

3. The process of claim 2, wherein said double sided tape comprise an interior film, said downward adhesive face being disposed under said interior film, and said upward facing adhesive face being disposed on top of said interior film.

4. The process of claim 1, wherein said adhesive layer is a homogeneous adhesive in which said downward adhesive face and said upward adhesive face are contiguous.

5. The process of claim 1, wherein said carrier film comprises adhesive sufficient to hold said fibers in place on said exposed portion.

6. The process of claim 5, wherein the adhesive force between said carrier film and fiber is less than the adhesive force between said adhesive layer and the fiber.

7. The process of claim 1, wherein said tail portion is terminated with at least one optical connector.

8. An optical flexible circuit comprising:
a carrier film;
an adhesive layer on a portion of said carrier film, said adhesive layer having a downward adhesive face and an upward adhesive face, said downward adhesive face and said carrier film being configured such that said carrier film is removable from said downward face without disruption of said downward adhesive face, said adhesive layer covering only a portion of said carrier film, leaving an exposed portion of said carrier film;
a plurality of fibers disposed on said carrier film in a pattern comprising at least one curved portion in which said fibers are curved, and at least one tail portion in which said fibers are essentially straight, said curved portion being disposed on said adhesive layer and said tail portion being disposed on said exposed portion; and
a coating over said fibers.

9. The optical flexible circuit of claim 8, wherein said adhesive layer is double sided tape.

10. The optical flexible circuit of claim 9, wherein said double sided tape comprises an interior film, said downward adhesive face being disposed under said interior film, and said upward facing adhesive face being disposed on top of said interior film.

11. The optical flexible circuit of claim 8, wherein said adhesive layer is a homogeneous adhesive in which said downward adhesive face and said upward adhesive face are contiguous.

12. The optical flexible circuit of claim 8, wherein said carrier film comprises adhesive sufficient to hold said fibers in place on said exposed portion.

13. The optical flexible circuit of claim 8 wherein said tail portion is terminated with at least one optical connector.

14. A method of using an optical flexible circuit comprising a carrier film, an adhesive layer on said carrier film, said adhesive layer having a downward adhesive face and an upward adhesive face, said downward adhesive face and said carrier film being configured such that said carrier film is removable from said downward adhesive face, said adhesive layer covering only a portion of said carrier film, leaving an exposed portion of said carrier film, and a plurality of fibers disposed on said carrier film in a pattern comprising at least one curved portion in which said fibers are curved, and at least one tail portion in which said fibers are essentially straight, said curved portion being disposed on said adhesive layer and said tail portion being disposed on said exposed portion to define an optical circuit; and a coating over said fibers, said method comprising:
removing said carrier from said downward adhesive layer to expose said downward adhesive face; and
affixing said downward adhesive face to a surface to secure said optical circuit to said surface.

15. The method of claim 14, wherein said tail portion of said fibers are terminated with at least one optical connector and wherein, after affixing said downward adhesive face, mating said optical connector with a mating connectors.

16. The method of claim 14, wherein, after affixing said downward adhesive face, splicing at least a portion of said fibers of said tail portion with mating fibers.

* * * * *